(12) United States Patent
Govari

(10) Patent No.: US 12,383,185 B2
(45) Date of Patent: Aug. 12, 2025

(54) IDENTIFYING A VORTEX IN AN ELECTRO-ANATOMICAL MAP

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 18/910,532

(22) Filed: Oct. 9, 2024

(65) Prior Publication Data

US 2025/0032036 A1   Jan. 30, 2025

Related U.S. Application Data

(63) Continuation of application No. 17/409,429, filed on Aug. 23, 2021, now abandoned.

(51) Int. Cl.
*A61B 5/367* (2021.01)
*A61B 5/00* (2006.01)
*A61B 5/339* (2021.01)

(52) U.S. Cl.
CPC ............. *A61B 5/367* (2021.01); *A61B 5/339* (2021.01); *A61B 5/7282* (2013.01); *A61B 5/742* (2013.01)

(58) Field of Classification Search
CPC ....... A61B 5/367; A61B 5/339; A61B 5/7282; A61B 5/742
See application file for complete search history.

(56) References Cited

U.S. PATENT DOCUMENTS

| | | |
|---|---|---|
| 5,391,199 A | 2/1995 | Shlomo |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Shlomo et al. |
| 9,545,210 B2 | 1/2017 | Lo et al. |
| 2002/0065455 A1 | 5/2002 | Shlomo et al. |
| 2003/0120150 A1 | 6/2003 | Govari |

(Continued)

FOREIGN PATENT DOCUMENTS

WO     1996005768 A1     2/1996

OTHER PUBLICATIONS

Kim YH et al.; 2019 APHRS expert consensus statement on three-dimensional mapping systems for tachycardia developed in collaboration with HRS, EHRA, and LAHRS. J Arrhythm. Mar. 9, 2020;36(2):215-270. (Year: 2020).*

(Continued)

*Primary Examiner* — Jennifer Pitrak McDonald
*Assistant Examiner* — Christopher J Mutchler
(74) *Attorney, Agent, or Firm* — Dergosits & Noah LLP; Todd A. Noah

(57) ABSTRACT

A system for identifying vortices in a vector map including multiple vectors, the system includes a processor and an output device. The processor is configured to: (i) define one or more closed loops on the vector map, and (ii) for each closed loop, identify a plurality of the vectors that cross the closed loop, calculate a vector sum of the identified vectors, and decide based on the vector sum whether a vortex is located inside the closed loop. The output device is configured to indicate one or more identified vortices to a user.

12 Claims, 2 Drawing Sheets

(56) References Cited

U.S. PATENT DOCUMENTS

2004/0068178 A1 4/2004 Govari
2019/0104958 A1 4/2019 Rappel et al.
2020/0281491 A1 9/2020 Han et al.
2020/0375489 A1 12/2020 Govari

OTHER PUBLICATIONS

Kurian, T. et al.; "Characterization of Drivers in Patients with Persistent Atrial Fibrillation to Identify Substrate Based Rotor Ablation Targets;" The Journal of Innovations in Cardiac Rhythm Management, 6 (2015), 2153-2161 (Year: 2015).*
Search Report from corresponding European Patent Application No. 22191397.3 dated Jan. 25, 2023.
Hu et al., "Tropical Cyclone Center Automatic Determination Model Based on HY-2 and QuikSCAT Wind Vector Products," IEEE Transactions on Geoscience and Remote Sensing, USA, 57(2), Feb. 1, 2019, pp. 709-721.
Bhakta et al., Principles of Electroanatomic Mapping, Indian Pacing and Electrophysiology Journal, 8(1), Feb. 1, 2008, pp. 32-50.
Dictionary.net, Definition of "Automatically," https://www.dictionary.net/automatically, accessed Feb. 13, 2024.
Merriam-Webster.com, Definition of "real time," https://www.merriam-webster.com/dictionary/real%20time, accessed Feb. 13, 2024.
TheFreeDictionary.com, Definition of "Based (up)on," https://idioms.thefreedictionary.com/based+upon, accessed Feb. 13, 2024.
Friedman, Paul A., Novel mapping techniques for cardiac electrophysiology, Heart, 87(6), Fune 2022, pp. 575-582.
Dallet et al., "Cardiac Propagation Pattern Mapping with Vector Field for Helping Tachyarrhythmias Diagnosis with Clinical Tridimensional Electro-Anatomical Mapping Tools," IEEE Transactions in Biomedical Engineering, Feb. 2019, 66(2), pp. 373-382.
Zaman, Junaid A.B. et al., Rotor mapping and ablation to treat atrial fibrillation, Curr Opin Cardiol., Jan. 2015, 30(1), pp. 24-32.
Rolf et al., "Electroanatomical Mapping of Atrial Fibrillation: Review of the Current Techniques and Advances," Journal of Atrial Fibrillation, 7(4), Dec. 2014-Jan. 2015, pp. 57-68.
"The Carto 3 System," Biosense Webster, Inc., 2019.
Decision to grant a European patent pursuant to Article 97(1) EPC dated Aug. 2, 2024.

* cited by examiner

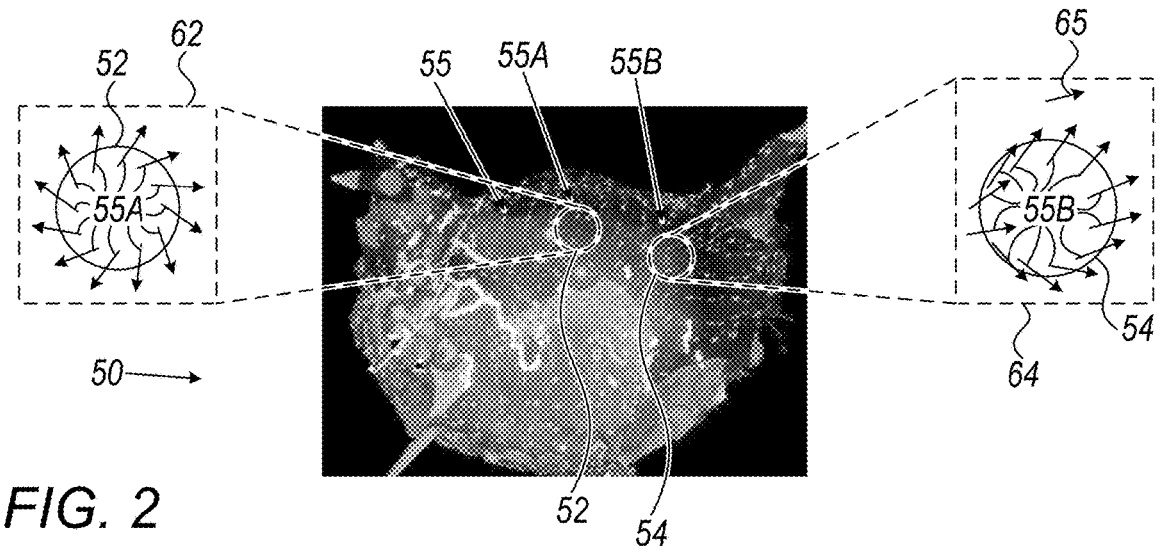

| Define, on an electro-anatomical (EA) map having multiple vectors, one or more circles | ~100 |

| For each circle, identify a plurality of the vectors that cross a perimeter of the circle, calculate a vector sum of the identified vectors, and decide, based on the vector sum, whether a vortex is located inside the circle | ~102 |

| Present to a user, an output indicative of one or more vortices identified in the EA map | ~104 |

IDENTIFYING A VORTEX IN AN ELECTRO-ANATOMICAL MAP

CROSS-REFERENCE TO RELATED APPLICATIONS

This application is a continuation of U.S. patent application Ser. No. 17/409,429, filed Aug. 23, 2021, the entire contents of which is incorporated herein by reference as if set forth in full herein.

FIELD OF THE INVENTION

The present invention relates generally to medical devices, and more particularly to methods and systems for identifying a vortex in an electro-anatomical map.

BACKGROUND OF THE INVENTION

Various techniques for identifying arrhythmias in electro-anatomical maps have been published.

For example, U.S. Patent Application Publication No. 2019/0104958 describes methods and systems for determination and mapping of vector fields which characterize wavefront motion through space and time. The inventive methods and systems utilize data from spatially distributed locations and maps wavefront vector flow fields in an entirely automated manner. These maps can be used to characterize the activation as planar, centrifugal, or rotational. Further, the strength of rotation or divergence is determined from these fields and can be used to select spatial points of significantly increased rotational or focal activity. As applied to electrophysiological data recorded during heart rhythm disorders in patients, the inventive method provides a means of visual interpretation of complex activation maps. The information related to the strength and location of rotation and centrifugal activity during episodes of arrhythmia can guide therapies designed to treat such disorders.

U.S. Patent Application Publication No. 2020/0375489 describes a method including receiving, in a processor, a two-dimensional (2D) electroanatomical (EA) map of an interior surface of at least a portion of a cavity of an organ of a patient, the 2D EA map including electrophysiological (EP) values measured at respective locations on the interior surface. A complex analytic function is fitted to a set of the EP values that were measured in a given region of the 2D EA map. A singularity is identified in the fitted complex analytic function. The region is projected onto a three-dimensional (3D) EA map of the interior surface. At least part of the 3D EA map is presented to a user, including indicating an arrhythmogenic EP activity at a location on the 3D EA map corresponding to the singularity identified in the fitted complex analytic function.

SUMMARY OF THE INVENTION

An embodiment of the present invention that is described herein provides a system for identifying vortices in a vector map including multiple vectors, the system includes a processor and an output device. The processor is configured to: (i) define one or more closed loops on the vector map, and (ii) for each closed loop, identify a plurality of the vectors that cross the closed loop, calculate a vector sum of the identified vectors, and decide based on the vector sum whether a vortex is located inside the closed loop. The output device is configured to indicate one or more identified vortices to a user.

In some embodiments, at least one of the closed loops includes a circle. In other embodiments, the processor is configured to decide that the vortex is located inside the closed loop in response to the vector sum being less than a threshold. In yet other embodiments, the processor is configured to adjust one or both of a size and a shape of at least one of the closed loops, so as to identify the vortex.

In an embodiment, the processor is configured to adjust a position of at least one of the closed loops, so as to identify the vortex. In another embodiment, the vector map includes an electro-anatomical (EA) map of a patient heart, the multiple vectors are indicative of electrical signals propagating over a surface of the patient heart, and by identifying the vortex, the processor is configured to identify one or more re-entrant arrhythmias in the patient heart.

There is additionally provided, in accordance with an embodiment of the present invention, a method for identifying vortices in a vector map including multiple vectors, the method includes defining one or more closed loops on the vector map, and for each closed loop, identifying a plurality of the vectors that cross the closed loop. A vector sum of the identified vectors is calculated, and based on the vector sum, deciding whether a vortex is located inside the closed loop. One or more identified vortices are indicated to a user.

BRIEF DESCRIPTION OF THE DRAWINGS

The present invention will be more fully understood from the following detailed description of the embodiments thereof, taken together with the drawings in which:

FIG. 2 is a schematic, pictorial illustration of a three-dimensional (3D) electro-anatomical (EA) map having wave vectors, in accordance with an exemplary embodiment of the present invention; and FIG. 3 is a flow chart that schematically illustrate a method for identifying vortices in a vector map comprising multiple wave vectors, in accordance with exemplary embodiments of the present invention.

DETAILED DESCRIPTION OF EMBODIMENTS

Overview

Figure 1:
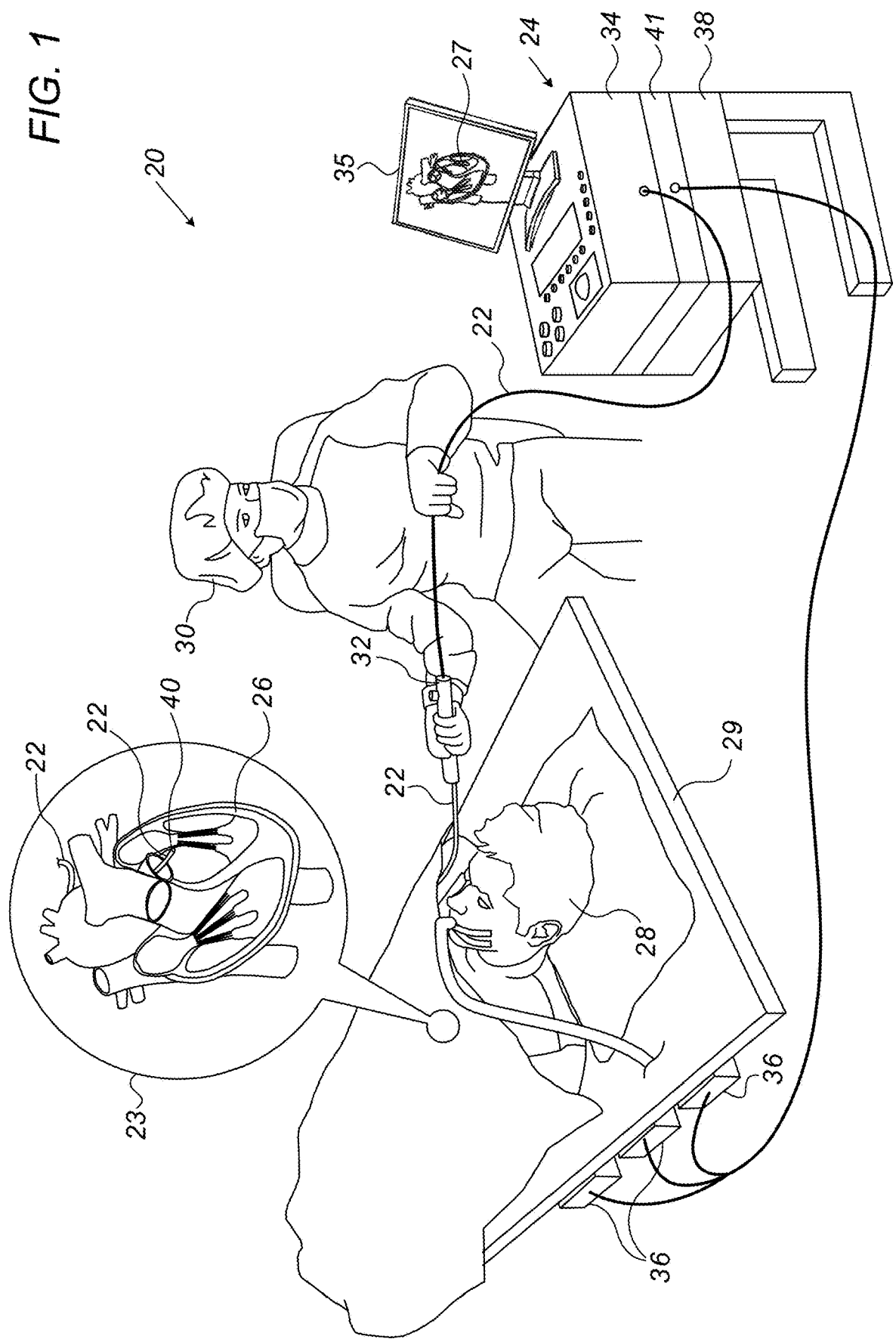
FIG. 1 is a schematic, pictorial illustration of a catheter-based tracking and ablation system, in accordance with an exemplary embodiment of the present invention.

Re-entrant arrhythmias occur in a patient heart when an electrical impulse recurrently travels in a tight circle within the heart, rather than moving from one end of the heart to the other end, and then stopping. When conducting electro-anatomical (EA) mapping of at least a portion of the patient heart, at least some re-entrant arrhythmias may appear as vortices of wave vectors produced during the EA mapping. When a vortex occurs in the patient heart, the directions of the wave vectors are typically distributed symmetrically and therefore, the wave vectors associated with the vortex are mutually canceled.

In principle, an experienced cardiac electrophysiologist, also referred to herein as a physician, may identify one or more vortices by visually inspecting the arrangement of wave vectors presented on an EA map. However, an increasing number of data points and wave vectors presented over EA maps, may conceal from the physician, one or more vortices. Moreover, a qualitative identification of a vortex (using a visual assessment) may result in, for example, a different assessment of the same anatomical phenomena, among different physicians. Therefore, it is important to develop a quantitative criterion for identifying a vortex in an EA map.

Embodiments of the present invention that are described hereinbelow provide improved techniques for identifying vortices based on wave vectors of a vector map presented over an EA map of a patient heart. In the context of the present disclosure and in the claims, the terms "vector" and "wave vector" are used interchangeably and refer to display objects indicative of electrical signals propagating over a surface of the patient heart.

In some embodiments, the EA map comprises various types of display objects, such as but not limited to wave vectors of a vector map, which are presented over an anatomical map of the patient heart.

In some embodiments, a system, which comprises a processor and an output device, is configured to identify vortices in the vector map having the plurality of wave vectors.

In some embodiments, the processor is configured to define one or more closed loops on the vector map, the closed loops may have a shape of a circle or any other suitable shape. When a vortex appears within the closed loop, the directions of the wave vectors that cross the closed loop shape are expected to be distributed symmetrically around the closed loop and therefore will cancel each other out when summed.

In some embodiments, for each closed loop, the processor is configured to identify a plurality of the vectors that cross the closed loop. The processor is further configured to calculate a vector sum of the identified vectors, and to decide based on the vector sum, whether a vortex is located inside the closed loop.

In some embodiments, the processor is configured to hold a threshold, and to compare between the vector sum and the threshold. Based on the comparison, the processor is configured to decide that a vortex is located inside the closed loop when the vector sum is smaller than the threshold.

In some embodiments, the processor is configured to adjust at least one of the size, the shape, and the position of the closed loop, so as to identify one or more vortices in the vector map presented over the EA map. The processor is further configured to produce an output indicative of the one or more identified vortices, and the position of each identified vortex.

In some embodiments, the output device, e.g., a display, is configured to present the output produced by the processor on the EA map, using any suitable display objects. As described above, the wave vectors of the vector map are indicative of electrical signals propagating over a surface of the patient heart. Thus, by identifying the vortex, the processor is configured to identify one or more re-entrant arrhythmias that occurred in the patient heart.

The disclosed techniques provide cardiac electrophysiologists with identification and mapping of vortices in electro-anatomical (EA) maps of patient heart. The identification is based on a quantitative analysis of selected sections of the heart, which are suspected of having re-entrant arrhythmias. Moreover, as opposed to the cardiac electrophysiologist, who may err in identifying a vortex due to a congestion of information displayed over the EA map, the disclosed techniques improve the identification accuracy of cardiac vortices, in response to an increase in the amount of electrophysiological measurements presented over the EA map of the heart.

System Description

FIG. 1 is a schematic, pictorial illustration of a catheter-based tracking and ablation system 20, in accordance with an exemplary embodiment of the present invention.

In some embodiments, system 20 comprises a catheter 22, in the present example a cardiac catheter, and a control console 24. In the embodiment described herein, catheter 22 may be used for any suitable therapeutic and/or diagnostic purposes, such as sensing electro-anatomical signals and/or ablation of tissue in a heart 26 of a patient 28.

In some embodiments, console 24 comprises a processor 34, typically a general-purpose computer, with suitable front end and interface circuits for receiving signals via catheter 22 and for controlling the other components of system 20 described herein. Console 24 further comprises a user display 35, which is configured to receive from processor 34 a map 27 of heart 26, and to display map 27.

In some embodiments, map 27 may comprise any suitable type of three-dimensional (3D) anatomical map produced using any suitable technique. For example, the anatomical map may be produced using an anatomical image produced by using a suitable medical imaging system, or using a fast anatomical mapping (FAM) techniques available in the CARTO™ system, produced by Biosense Webster Inc. (Irvine, Calif.), or using any other suitable technique, or using any suitable combination of the above.

Reference is now made to an inset 23. In some embodiments, prior to performing an ablation procedure, a physician 30 inserts catheter 22 through the vasculature system of a patient 28 lying on a table 29, so as to perform electro-anatomical (EA) mapping of tissue in question of heart 26.

In some embodiments, catheter 22 comprises a distal-end assembly 40 having multiple sensing electrodes (not shown). For example, distal-end assembly 40 may comprise: (i) a basket catheter having multiple splines, each spline having multiple sensing electrodes, (ii) a balloon catheter having multiple sensing electrodes disposed on the surface of the balloon, or (iii) a focal catheter having multiple sensing electrodes. Each sensing electrode is configured to produce, in response to sensing electrophysiological (EP) signals in tissue of heart 26, one or more signals indicative of the sensed EP signals.

In some embodiments, the proximal end of catheter 22 is connected, inter alia, to interface circuits (not shown), so as to transfer these signals to processor 34 for performing the EA mapping. In some embodiments, during the EA mapping, the signals produced by the sensing electrodes of distal-end assembly 40 may comprise thousands of data points, e.g., about 50,000 data points or even more, which may be stored in a memory 38 of console 24. Based on the data points, processor 34 is configured to present on map 27, wave vectors, also referred to herein as vectors (shown in FIG. 2 below), which are indicative of electrical signals propagating over the surface of heart 26.

In some embodiments, based on the presented vectors, physician 30 and/or processor 34, may identify one or more types of arrhythmias that occurred in heart 26. Moreover, physician 30 may determine one or more sites for treating the arrhythmias, e.g., by ablating tissue in heart 26. However, physician 30 may have difficulties to review and analyze the aforementioned large number of data points and vectors, which may prolong the duration of the ablation procedure. Moreover, the large amount of data points and vectors may confuse physician 30, and therefore, may reduce the quality of the EA analysis and corresponding treatment, e.g., tissue ablation.

In the context of the present disclosure and in the claims, the terms "about" or "approximately" for any numerical values or ranges indicate a suitable dimensional tolerance that allows the part or collection of components to function for its intended purpose as described herein.

In some cases, heart 26 may have one or more sites of re-entrant arrhythmias, also referred to herein as "re-entry." In some embodiments, processor 34 is configured to identify, in an EA map (e.g., map 27) of heart 26, multiple vectors arranged in a shape, which is indicative of a re-entry. Techniques for identifying re-entrant arrhythmias are described in detail in FIGS. 2 and 3 below.

In other embodiments, catheter 22 may comprise one or more ablation electrodes (not shown) coupled to distal-end assembly 40. The ablation electrodes are configured to ablate tissue at a target location of heart 26, which is determined based on the analysis of the EA mapping of the tissue in question of heart 26. After determining the ablation plan, physician 30 navigates distal-end assembly 40 in close proximity to the target location in heart 26 e.g., using a manipulator 32 for manipulating catheter 22. Subsequently, physician 30 places one or more of the ablation electrodes in contact with the target tissue, and applies, to the tissue, one or more ablation signals. Additionally, or alternatively, physician 30 may use any different sort of suitable catheter for ablating tissue of heart 26 so as to carry out the aforementioned ablation plan.

In some embodiments, the position of distal-end assembly 40 in the heart cavity is measured using a position sensor (not shown) of a magnetic position tracking system. In the present example, console 24 comprises a driver circuit 41, which is configured to drive magnetic field generators 36 placed at known positions external to patient 28 lying on table 29, e.g., below the patient's torso. The position sensor is coupled to the distal end and is configured to generate position signals in response to sensed external magnetic fields from field generators 36. The position signals are indicative of the position the distal end of catheter 22 in the coordinate system of the position tracking system.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publication Nos. 2002/0065455 A1, 2003/0120150 A1 and 2004/0068178 A1, whose disclosures are all incorporated herein by reference.

In some embodiments, the coordinate system of the position tracking system are registered with the coordinate systems of system 20 and map 27, so that processor 34 is configured to display, the position of distal-end assembly 40, over the anatomical or EA map (e.g., map 27).

In some embodiments, processor 34, typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

This particular configuration of system 20 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of medical systems.

Automatically Identifying Vortices Indicative of Re-Entrant Arrhythmias

FIG. 2 is a schematic, pictorial illustration of a three-dimensional (3D) electro-anatomical (EA) map 50, in accordance with an exemplary embodiment of the present invention. EA map 50 comprises a 3D anatomical map of at least a portion of heart 26, and has, inter alia, multiple vectors 55 indicative of electrical signals propagating over the surface of heart 26. EA Map 50, which is also referred to herein as a map 50, for brevity, may replace for example, map 27 of FIG. 1 above.

In some cases, heart 26 may have re-entrant, or other sorts of arrhythmias. Re-entrant arrhythmias typically occur when an electrical impulse recurrently travels in a closed loop, typically in a tight circle within heart 26, rather than moving from one end of the heart to the other end, and then stopping. As a sort of re-entry, vortices of excitation in the myocardium of heart 26, are considered to be a mechanism of life-threatening cardiac arrhythmias. In principle, physician 30 may identify one or more vortices by visually inspecting the arrangement of wave vectors 55 presented over EA map 50. However, the increased number of data points and wave vectors 55 in the EA maps (e.g., EA maps 27 and 50 of FIGS. 1 and 2, respectively), may conceal one or more vortices from physician 30. Moreover, a qualitative identification of a vortex (using a visual inspection) may result in, for example, a different assessment of the same anatomical phenomena, among different physicians. Therefore, it is important to develop a quantitative criterion for identifying vortices in EA map 50.

In some embodiments, processor 34 is configured to define one or more closed loops, in the present example, circles 52 and 54, on EA map 50. As described above, EA map 50 comprises a vector map having multiple vectors 55. In some embodiments, circles 52 and 54 may be defined within a section of heart 26, which is selected by physician 30 on EA map 50. Additionally, or alternatively, processor 34 is configured to scan at least a portion of EA map 50, and based on the arrangement of vectors 55 in the scanned area(s), processor 34 may define the position, the size, the shape, and the amount of the closed loops defined and placed over EA map 50.

Reference is now made to insets 62 and 64 showing circles 52 and 54, respectively. In some embodiments, circle 52 is defined on EA map 50 such that multiple vectors 55A, from among vectors 55, cross the perimeter of circle 52. Similarly, circle 54 is defined on EA map 50, such that multiple vectors 55B, from among vectors 55, cross the perimeter of circle 54.

In some embodiments, processor 34 is configured to identify vectors 55A and 55B that cross circles 52 and 54, respectively. Moreover, processor 34 is configured to calculate, for each of the aforementioned circles, a vector sum of the identified vectors, and to decide, based on the vector sum, whether a vortex is located inside the respective circle.

In some embodiments, processor 34 may hold a threshold, which may be predefined by physician 30 as a percentage of a normalized range of vectors 55A and 55B that cross circles 52 and 54 (e.g., smaller than about 10% of the normalized range) that defines whether or not the vector sum is indicative of a vortex within the circle, or within any other shape of a closed loop defined by the processor (e.g., an ellipse).

In such embodiments, processor 34 is configured to compare between the vector sum and the threshold, and in case the vector sum is smaller than the threshold, processor 34 identifies a vortex within the respective close loop.

Reference is now made again to inset 62. When a vortex occurs in heart 26, the directions of vectors 55A are typically distributed symmetrically and therefore, vectors 55A are mutually canceled. In the example of circle 52, the magnitude of the vector sum of vectors 55A is about zero, which is smaller than the threshold. In some embodiments, based on the vector sum and the threshold, processor 34 is configured to decide that a vortex is located inside circle 52.

In some embodiments, processor 34 is configured to produce an output indicating that the vortex is identified inside circle 52. Moreover, display 35 or any other suitable output device, may display the identified vortex to physician 30, e.g., at the original position of circle 52 on EA map 50.

Reference is now made back to inset 64. In the example of circle 54, a vector 65 shows a calculated vector sum of vectors 55B having a direction and magnitude. In the present example, the magnitude of vector 65 is larger than about 10 percent of the normalized range of vectors 55B, which is larger than the threshold. Therefore, based on the vector sum and the threshold, processor 34 is configured to decide that no vortex is located inside circle 54. Moreover, processor 34 is configured to output, to display 35 or to any other suitable output device, an indication that the vector sum of wave vectors 55B is propagating across heart 26 in the direction of vector 65.

In other embodiments, in addition to or instead of circles 52 and 54, processor 34 is configured to define on EA map 50, other sorts of closed loops having any suitable shape and/or size. Moreover, processor 34 is configured to adjust the size and/or the shape of one or more of the closed loops, so as to identify one or more vortices in EA map 50.

In other embodiments, processor 34 is configured to adjust the position of a closed loop (e.g., circle 54) on EA map 50, so as to identify a vortex at the adjusted position of circle 54 on EA map 50. Moreover, processor 34 is configured to adjust any combination of size, shape, and position of one or more of the closed loops, in order to check whether or not EA map 50 has additional vortices.

In some embodiments, display 35 (or any other suitable type of output device) is configured to indicate one or more identified vortices to physician 30 (or to any other user of system 20), using any suitable technique. For example, a pop-up displayed at the position of the identified vortex, a color applied to the closed loop (e.g., circle 52) that is indicative of an identified vortex, a list with positions and properties of the identified vortices, or any other suitable type of indication.

In some embodiments, based on the presence of one or more vortices identified by processor 34, physician 30 can: (i) decide whether or not heart 26 has one or more re-entrant arrhythmias, and (ii) based on the position of each re-entrant arrhythmias, physician 30 may determine a treatment, such as but not limited to target location(s), and parameters of radiofrequency (RF) ablation, in tissue of heart 26.

In other embodiments, processor 34 is configured to: (i) define multiple elements at different positions on EA 50, (ii) identify vectors, within an area surrounded by the multiple elements, or along a perimeter surrounding the multiple elements, and (iii) calculate a vector sum of the vectors, so as to decide (based on the vector sum), whether a vortex is located inside the area surrounded by three or more of the multiple elements.

FIG. 3 is a flow chart that schematically illustrates a method for identifying vortices in EA map 50 having multiple vectors 55, 55A and 55B, in accordance with exemplary embodiments of the present invention.

The method begins at a circles definition step 100, with processor 34 (i) receiving EA map 50 having multiple vectors 55, 55A and 55B, and (ii) defining on EA map 50, one or more closed loops, such as but not limited to circles 52 and 54, as described in detail in FIG. 2 above.

At a vortex identification step 102, for each of the defined circles, processor 34 (i) identifies a plurality of the vectors that cross a perimeter of the circle, (ii) calculates a vector sum of the identified vectors, and (iii) decides, based on the vector sum, whether a vortex is located inside the circle. In some embodiments, processor 34 holds a threshold and compares between the vector sum and the threshold, in order to decide whether a vortex is located inside the circle, as described in detail in FIG. 2 above. In the example of circle 52, the vector sum is smaller than the threshold, so that a vortex is identified within circle 52. In the example of circle 54, the vector sum is larger than the threshold, so that no vortex is identified within circle 54.

At a presentation step 104 that concludes the method, processor 34 presents to physician 30 (e.g., on display 35), an output indicative of one or more vortices identified in EA map 50. Several embodiments related to the presentation of the vortices are described in detail FIG. 2 above.

In some embodiments, EA map 50 comprises a 3D anatomical map of at least a portion of heart 26, and vectors 55, 55A and 55B comprise wave vectors indicative of electrical signals propagating over the surface of heart 26, as described in FIG. 2 above. In some embodiments, processor 34 is configured to adjust one or both of the size and the shape of at least one of the closed loops (e.g., circles 52 and 54), so as to identify the vortex. Moreover, processor 34 is configured to adjust the position of at least one of the closed loops (e.g., circle 54), so as to identify an additional vortex. As described in detail in FIG. 2, based on the identification of the one or more vortices, processor is configured to identify one or more re-entrant arrhythmias in heart of patient 28. In response to identifying the one or more re-entrant arrhythmias, physician 30 may determine a treatment, such as but not limited to an RF ablation of the heart tissue, for treating the re-entrant arrhythmias.

Although the embodiments described herein mainly address identification of one or more vortices indicative of re-entrant arrhythmias in the patient heart, the methods and systems described herein can also be used in other cardiac applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for identifying vortices in an electro-anatomical vector map of a patient heart comprising multiple vectors indicative of electrical signals propagating over a surface of the patient heart, the system comprising:
  a processor, which is configured to:
    receive, from a catheter comprising a distal end assembly having multiple sensing electrodes, one or more signals indicative of the electrical signals propagating over the surface of the patient heart;
    produce the electro-anatomical vector map based on the one or more signals;
    define one or more closed loops on the electro-anatomical vector map; and
    identify, for each closed loop, a plurality of the vectors that cross the closed loop, calculate a vector sum of the identified vectors, and determine based on the vector sum whether a vortex indicative of a re-entrant arrythmia is located inside the closed loop;
    cause, in response to a determination that one or more vortices are located in respective one or more closed loops, the one or more identified vortices to be displayed to a user on an output device; and
    cause, based on the determination that one or more vortices are located in respective one or more closed loops, ablation of the heart tissue by controlling the catheter to, at least one of: i) ablate target locations in the heart tissue corresponding to the one or more vortices, or ii) ablate the heart tissue in accordance with ablation parameters for treating the re-entrant arrythmia indicated by the one or more vortices.

2. The system according to claim 1, wherein at least one of the closed loops comprises a circle.

3. The system according to claim 1, wherein the processor is configured to decide that the vortex is located inside the closed loop in response to the vector sum being less than a threshold.

4. The system according to claim 1, wherein the processor is configured to adjust one or both of a size and a shape of at least one of the closed loops, so as to identify the vortex.

5. The system according to claim 1, wherein the processor is configured to adjust a position of at least one of the closed loops, so as to identify the vortex.

6. The system according to claim 1, wherein, by identifying the vortex, the processor is configured to identify one or more re-entrant arrhythmias in the patient heart.

7. A method, implemented by a processor, for identifying vortices in an electro-anatomical vector map of a patient heart comprising multiple vectors indicative of electrical signals propagating over a surface of the patient heart, the method comprising:
  defining one or more closed loops on the electro-anatomical vector map, and for each closed loop, identifying a plurality of the vectors that cross the closed loop;
  calculating a vector sum of the identified vectors, and determining based on the vector sum whether a vortex indicative of a re-entrant arrythmia is located inside the closed loop;
  indicating, in response to a determination that one or more vortices are located in respective one or more closed loops, the one or more identified vortices to a user; and
  causing, based on the determination that one or more vortices are located in respective one or more closed loops, ablation of the heart tissue by controlling the catheter to, at least one of: i) ablate target locations in the heart tissue corresponding to the one or more vortices, or ii) ablate the heart tissue in accordance with ablation parameters for treating the re-entrant arrythmia indicated by the one or more vortices.

8. The method according to claim 7, wherein defining the closed loops comprises defining at least a circle among the closed loops.

9. The method according to claim 7, wherein deciding based on the vector sum comprises deciding that the vortex is located inside the closed loop in response to the vector sum being less than a threshold.

10. The method according to claim 7, and comprising adjusting one or both of a size and a shape of at least one of the closed loops, so as to identify the vortex.

11. The method according to claim 7, and comprising adjusting a position of at least one of the closed loops, so as to identify the vortex.

12. The method according to claim 7, wherein, identifying the vortex comprises identifying one or more re-entrant arrhythmias in the patient heart.

* * * * *